United States Patent [19]

Cross et al.

[11] 4,448,781

[45] May 15, 1984

[54] N-BENZYL-IMIDAZOLES AS SELECTIVE INHIBITORS OF THE THROMBOXANE SYNTHETASE ENZYME

[75] Inventors: Peter E. Cross, Canterbury; Roger P. Dickinson, Dover, both of England

[73] Assignee: Pfizer Inc., New York, N.Y.

[21] Appl. No.: 286,808

[22] Filed: Jul. 27, 1981

Related U.S. Application Data

[62] Division of Ser. No. 110,711, Jan. 9, 1980.

[30] Foreign Application Priority Data

Jan. 19, 1979 [GB] United Kingdom ............... 7902114

[51] Int. Cl.³ .................. C07D 257/04; A61K 31/41
[52] U.S. Cl. .................................... 424/269; 548/252
[58] Field of Search ............... 548/252, 335; 424/269

[56] References Cited

U.S. PATENT DOCUMENTS

| | | | |
|---|---|---|---|
| 3,498,999 | 3/1970 | Buchanan et al. | 548/252 |
| 4,118,487 | 10/1978 | Regal et al. | 548/335 |
| 4,183,742 | 1/1980 | Sasse et al. | 546/210 |

FOREIGN PATENT DOCUMENTS

| | | |
|---|---|---|
| 271776 | 2/1951 | Switzerland . |
| 1510016 | 5/1978 | United Kingdom . |
| 2031408 | 4/1980 | United Kingdom . |

OTHER PUBLICATIONS

Buchanan et al., J. Med. Chem., vol. 12, Nov. 1969, p. 1001.
Tai et al., "Biochemical and Biophysical Res. Comm., vol. 80, No. 1, 1978, pp. 235–243.
Johnson et al., J. Med. Chem. 12, 1024 (1969).
Baggaley et al., J. Med. Chem. 18, 833 (1975).

Primary Examiner—Paul M. Coughlan, Jr.
Assistant Examiner—D. B. Springer
Attorney, Agent, or Firm—Connolly and Hutz

[57] ABSTRACT

The N-(substituted benzyl) imidazoles are selective enzyme inhibitors and thus are useful in the treatment of heart disease, circulatory and vascular problems.

6 Claims, No Drawings

N-BENZYL-IMIDAZOLES AS SELECTIVE INHIBITORS OF THE THROMBOXANE SYNTHETASE ENZYME

CROSS REFERENCE TO RELATED APPLICATION

This application is a division of co-pending application Ser. No. 110,711, filed Jan. 9, 1980.

BACKGROUND

This invention relates to certain imidazole derivatives and in particular to a series of N-benzylimidazoles being substituted in the phenyl ring with acidic and polar groupings. Such compounds are able to selectively inhibit the action of the thromboxane synthetase enzyme without significantly inhibiting the action of the prostacyclin synthetase or cyclooxygenase enzymes. The compounds may thus be useful in, for example, the treatment of thrombosis, ischaemic heart disease, stroke, transient ischaemic attack, migraine and the vascular complications of diabetes.

SUMMARY

According to the invention there are provided compounds of the general formula:

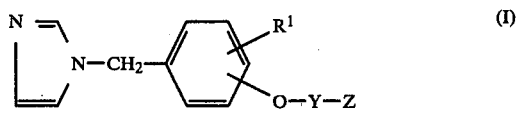
(I)

wherein
$R^1$ is hydrogen, $C_1$–$C_4$ lower alkyl, $C_1$–$C_4$ lower alkoxy or halogen,
Y is $(CH_2)_n$ where n is an integer of from 1 to 4, or a group of the formula:

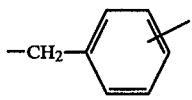

Z is $CO_2R^2$, $CONHR^3$, $CON(R^4)_2$, CN or tetrazolyl,
$R^2$ is hydrogen or $C_1$–$C_4$ lower alkyl,
$R^3$ is hydrogen, $C_1$–$C_4$ lower alkyl or $C_2$–$C_4$ lower alkanoyl, each $R^4$ is $C_1$–$C_4$ lower alkyl or two groups $R^4$ together with the nitrogen atom to which they are attached form a pyrrolidino or piperidino group,
and the pharmaceutically acceptable acid addition salts thereof.

The invention also includes a pharmaceutical composition comprising a compound of the formula (I), or a pharmaceutically acceptable salt thereof, together with a pharmaceutically acceptable diluent or carrier.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable salt thereof, or a pharmaceutical composition comprising such a compound or salt together with a pharmaceutically acceptable diluent or carrier.

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate and p-toluene sulphonate salts.

In this specification "halogen" indicates fluorine, chlorine, bromine or iodine. Alkyl and alkoxy groups having 3 or more carbon atoms and alkanoyl groups having 4 carbon atoms may be straight or branched chain.

Preferred compounds of the invention are those in which $R^1$ is hydrogen or methyl, and Z is a group $CO_2H$ or $CONH_2$. In one preferred group of compounds Y is a $C_1$–$C_3$ alkylene chain particularly a methylene group. In a further preferred group of compounds Y is a benzyl group, particularly a 4-substituted benzyl group.

Particularly preferred compounds include:
2-(1-Imidazolymethyl)-4-methyl-phenoxyacetic acid
4-[2-(1-Imidazolymethyl)-4-methyl-phenoxy]butyramide
4-[2-(1-Imidazolylmethyl)-4-methyl-phenoxymethyl]-benzoic acid
4-(1-Imidazolylmethyl)phenoxyacetic acid
4-(1-Imidazolylmethyl)phenoxyacetamide and
3-(1-Imidazolylmethyl)phenoxyacetic acid.

DETAILED DESCRIPTION

The compounds of the invention may be prepared by a number of different routes. In one process according to the invention the compounds of the formula (I) may be prepared from a phenol of the formula:

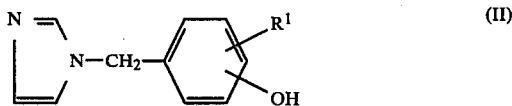
(II)

where $R^1$ is as previously defined, by first reacting with an alkali metal hydride and then reacting with a halide of the formula:

Hal—Y—Z         (III)

where Y and Z are as previously defined and Hal means chlorine, bromine or iodine.

The reaction is conveniently performed by adding one equivalent of the alkali metal hydride, e.g. sodium hydride to a solution of the phenol (II) in a dry inert organic solvent, e.g. N,N-dimethylformamide. The hydride is conveniently used in the form of a dispersion in a mineral oil. The reaction mixture is stirred at room temperature and the initial reaction is geneally complete within one or two hours. If the reaction is slow, however, the reaction mixture may be heated, e.g. at 100° C. for a further period of 30–60 minutes, to ensure that all the sodium hydride has reacted and evolution of hydrogen has ceased.

The solution is cooled and the halide (III) is added, preferably in an amount of 1 equivalent or a slight (e.g. 10%) excess. The reaction may be allowed to proceed to completion at room temperature but it is sometimes advantageous to heat the reaction mixture, e.g. at 100° C. to accelerate the reaction. The time taken for the reaction to go substantially to completion will naturally depend on the precise conditions and temperature used and on the nature of the reactants.

We have found, however, that even with the less reactive compounds a period of 9 hours at 100° C. is generally sufficient to ensure that the reaction is substantially complete. The reaction product is worked-up in a conventional manner, e.g. by removal of the solvent under vacuum or by pouring the reaction mixture into water to precipitate the product. The crude product is purified by solvent extraction and washing and may be further purified, if desired, by crystallisation or chromatography.

Naturally certain of the groups Z may be obtained by chemical transformation reactions and these possibilities will be well known to those skilled in the art. Thus for example the compounds of the formula (I) where Z is a carboxyl group may be obtained via hydrolysis of the corresponding esters where Z is a group $CO_2R^2$ and $R^2$ is a lower alkyl group. Alternatively treatment of the esters with ammonia gives the amides where Z is $CONH_2$. The amides may alternatively be prepared via hydrolysis of the compound of formula (I) wherein Z is a cyano group using concentrated hydrochloric acid or, in the case of aromatic nitriles, alkaline hydrogen peroxide. Acid hydrolysis of the nitriles can also be used to yield the corresponding acids where Z is a carboxyl group. The acids may be further converted to a variety of derivatives by conventional methods, thus formation of the acid chloride e.g. by reaction with thionylchloride followed by reaction with ammonia or a $C_1$–$C_4$ lower alkylamine gives compounds where Z is $CONHR^3$ and $R^3$ is hydrogen or lower alkyl respectively, or alternatively reaction of the acid chloride with a di-lower alkylamine or with pyrrolidine or piperidine gives compounds where Z is $CON(R^4)_2$.

Again the acid may be reacted with N,N-carbonyldiimidazole and the adduct reacted with a lower alkylamine or amide to give N-substituted amido products.

Compound where Z is tetrazolyl are prepared from the cyano derivative by reaction with sodium azide and ammonium chloride. All these reactions are quite conventional and conditions for their performance will be well known to those skilled in the art.

The starting materials of formula (II) are generally known compounds obtainable by conventional techniques. Thus they may prepared from a phenol of the formula:

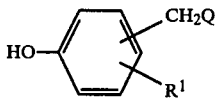

where $R^1$ is as previously defined and Q is a leaving group, e.g. a dimethylamino group or a halogen atom, by reaction with imidazole or, in the case of the meta-hydroxy-benzylimidazoles, by reaction with the sodium salt prepared by reaction of imidazole with sodium hydride.

The compounds of formula (I) have been found to selectively inhibit the action of the thromboxane synthetase enzyme without significantly affecting the action of the prostacyclin synthetase or cyclo-oxygenase enzymes.

Thus the compounds are of value in the treatment of a variety of clinical conditions which are characterized by an inbalance of prostacyclin/thromboxane $A_2$. For the reasons given below these conditions may include thrombosis, ischaemic heart disease, stroke, transient ischaemic attack, migraine and the vascular complications of diabetes.

Research work has established that in most tissues the major product of the arachidonic acid metabolism is either of two unstable substances, thromboxane $A_2$ ($TxA_2$) or prostacyclin ($PGI_2$). (Proc. Nat. Acad. Sci. U.S.A., 1975, 72, 2994, Nature, 1976, 263, 663, Prostaglandins, 1976, 12, 897). In most cases the prostaglandins $PGE_2$, $PGF_2$ and $PGD_2$ are comparatively minor by-products in this bio-synthetic pathway. The discovery of thromboxane $A_2$ and prostacyclin has significantly increased our understanding of vascular homeostasis, prostacyclin for instance is a powerful vasodilator and inhibitor of platelet aggregation and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685, Science, 1976, 17, Nature, 1978, 273, 765).

Thromboxane $A_2$ is synthetised by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18, Prostaglandins, 1978, 13, 3). Alteration of the prostacyclin/thromboxane balance in favour of the latter substance could result in platelet aggregation, vasospasm (Lancet, 1977, 479, Science, 1976, 1135, Amer. J. Cardiology, 1978, 41, 787) and an increased susceptibility to athero-thrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causitive agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extra-cerebral blood flow, in particular a pre-headache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250, J. Headache, 1977, 17, 101). Furthermore, it has now been postulated that not only is an abnormality of platelet function a major factor in the pathogenesis of migraine attacks but it is in fact their prime cause (Lancet (i), 1978, 501). Thus a drug that selectively modifies platelet function to inhibit thromboxane $A_2$ formation could be of considerable benefit in migraine therapy.

Abnormalities of platelet behaviour have been reported in patients with diabetes mellitus (Metabolism 1979, 28, 394, Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis—Implications for Therapy", Leeds U.K., April 1979). Also it has been shown that in rats with experimental diabetes vascular prostacyclin production is impaired and $TxA_2$ synthesis from the platelets is elevated (IV International Prostaglandin Conference, Washington, D.C. May 1979). Thus the imbalance between prostacyclin and $TxA_2$ is considered to be responsible for the microvascular complications of diabetes. A $TxA_2$-syntehtase inhibitor could therefore find clinical utility in preventing these vascular complications.

Aspirin and most other non-steroidal anti-inflammatory drugs inhibit the cyclo-oxygenase enzyme. The effect of this is to shut down the production of the $PGG_2/H_2$ endoperoxides and by so doing to reduce both the prostacyclin and thromboxane $A_2$ levels. Aspirin and aspirin-like drugs have been evaluated clinically for prevention of stroke and heart attack (New England and J. Med. 1978, 299, 53, B.M.J., 1978, 1188, Stroke, 1977, 8 301).

Although some encouraging results have been obtained with these drugs, a compound which specifically inhibits thromboxane $A_2$ formation leaving the biosynthesis of prostacyclin unimpaired would be more valuable in these clinical conditions (Lancet, (ii), 1978, 780).

The effect of the compounds of the formula (I) on the thromboxane synthetase enzyme, and the prostacyclin synthetase and cyclo-oxygenase enzymes has been measured by the following in vitro enzyme assays.

1. Cyclo-oxygenase

Ram seminal vesicle microsomes (Biochemistry, 1971, 10, 2372) are incubated with arachidonic acid (100 $\mu$M: 1 min.: 22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45, 451) which is superfusing a spirally-cut rabbit aorta strip (Nature, 1969, 223, 29). The ability of a compound to inhibit the enzyme is measured by comparing the increases in isometric tension produced by $PGH_2$ in the absence of the test compound, and following pre-incubation of the enzyme with the test compound for 5 minutes.

2. Prostacyclin ($PGI_2$) Synthetase

Pig aorta microsomes (Nature, 1976, 263, 663) are incubated (30 sec.: 22° C.) with $PGH_2$ produced as in 1) and aliquots bio-assayed as in 1. $PGI_2$ production is assessed indirectly by measuring the decrease in $PGH_2$-induced tension ($PGI_2$ itself does not contract the aorta). This decrease can be prevented completely by pre-incubation of the enzyme with the selective $PGI_2$ synthetase inhibitor, 15-hydroperoxy-arachidonic acid (Prostaglandins, 1976, 12, 715). The test compound is then pre-incubated with the enzyme for 5 minutes, and its ability to prevent the decrease in tension is measured.

3. Thromboxane $A_2$ ($TxA_2$) Synthetase

Indomethacin pre-treated human platelet microsomes (Science 1976, 193, 163) are incubated (2 min.: 0° C.) with $PGH_2$ (produced as in 1) and aliquots of the reaction mixture superfused over two rabbit aorta spirals which are separated by a delay coil (2 min.). The latter is required to allow the selective decay of the more unstable thromboxane $A_2$ (Proc. Nat. Acad. Sci., 1975, 72, 2994) thereby enabling the separate measurement of increased isometric tension due to the $TxA_2$ formed and the $PGH_2$ remaining. The test compound is pre-incubated with the enzyme for 5 minutes, and its ability to inhibit the thromboxane synthetase enzyme is measured as its reduction of the $TxA_2$ component of the isometric tension.

Compounds of the invention tested in this way have been shown to be capable of selectively inhibiting the thromboxane synthetase enzyme. The results of these tests are shown in the following Table, which gives the molar concentration of each compound which caused a 50% change in the effect of the relevant enzyme on isometric tension, i.e. caused a 50% inhibition of the action of that enzyme.

| | Molar concentration causing 50% inhibition of | | |
|---|---|---|---|
| Example | (1) thromboxane synthetase | (2) cyclo-oxygenase | (3) prostacyclin synthetase |
| 2 | $8.2 \times 10^{-9}$ | $>10^{-4}$ | $>10^{-4}$ |
| 4 | $2.4 \times 10^{-9}$ | $>10^{-4}$ | |
| 5 | $4.7 \times 10^{-8}$ | $>10^{-4}$ | |
| 7 | $1.0 \times 10^{-11}$ | | |
| 8 | $4.6 \times 10^{-8}$ | | $>10^{-4}$ |
| 24 | $4.5 \times 10^{-9}$ | | |

The results given in the Table show that all of the compounds tested caused a 50% inhibition of the thromboxane synthetase enzyme at a molar concentration of $1.0 \times 10^{-5}$ or less, and several caused 50% inhibition at concentrations of $10^{-8}$ or less.

Of the compounds tested for inhibition of the cyclooxygenase enzyme, none caused 50% inhibition at a molar concentration of $10^{-4}$ or less, their ability to inhibit that enzyme being at least 2,100 times less, than their ability to inhibit the thromboxane synthetase enzyme.

Of the compounds tested for inhibition of the prostacyclin synthetase enzyme, none caused 50% inhibition at a molar concentration less than 2,000 times greater than that at which they caused 50% inhibition of the thromboxane synthetase enzyme, i.e. they were all at least 2,000 times more potent as inhibitors of thromboxane synthetase than of prostacyclin synthetase.

It is expected that all the compounds of the invention when tested in this way will give results within the range of those already tested.

In addition to the above an in vitro assay for measuring the inhibition of human blood platelet aggregation has been described and this may be predictive of anti-thrombotic efficacy clinically (Lancet (ii), 1974, 1223, J. Exp. Med., 1967, 126, 171). Both clinically effective agents aspirin and sulphinpyrazone show inhibitory activity in vitro against a variety of aggregating agents in this test.

A number of in vivo tests in animals have also been described for evaluating potential anti-thrombotic drugs.

Intravenous injection of arachidonic acid causes death in rabbits by causing platelet clumping and embolisation in the lungs. Again both the clinically-effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Eaem, 1973, 30, 138).

The compounds may be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to tablets of the desired size. Capsules are typically prepared by granulating the ingredients together and filling them into hard gelatine capsules of the appropriate size to contain the ingredients.

The compounds may also be administered parenterally, for example by intramuscular, intravenous or subcutaneous injection. For parenteral administration, they are best used in the form of a sterile aqueous solution which may contain other solutes such as tonic and pH adjusters. The compounds may be added to distilled water and the pH adjusted to 3-6 using an acid such as citric, lactic or hydrochloric acid. Sufficient solutes such as dextrose or saline may be added to render the solution isotonic. The resulting solution may then be sterilized and filled into sterile glass vials of an appropriate size to contain the desired volume of solution. The compounds of the invention may also be administered by the infusion of a parenteral formulation as described above into a vein.

For oral administration to human patients, it is expected that the daily dosage level of a compound of the invention will be from 0.1 to 20 mg/kg per day for a typical adult patient (70 kg). For parenteral administration, it is expected that the daily dosage level of a compound of the formula (I) will be from 0.01-0.5 mg/kg per day, for a typical adult patient. Thus tablets or capsules can generally be expected to contain from 5 to 150 mg of the active compound for administration orally up to 3 times a day. Dosage units for parenteral administration can be expected to contain from 0.5-35 mg of the active compound. A typical vial could be a 10 ml vial containing 5 mg of the active compound in 6-10 ml of solution.

It should of course be appreciated that the physician in any event will determine the actual dosage which will be most suitable for the individual and it will vary with the age, weight and response of the patient. The above dosages are exemplary of the average patient, there may of course be individual cases where higher or lower dosage ranges are merited.

The preparation of the novel compounds of the invention is illustrated by the following Examples:

EXAMPLE 1

(A) 1-(2-Hydroxy-5-methyl)benzylimidazole

A solution of 2-dimethylaminoethyl-4-methylphenol (4.95 g) and imidazole (2.04 g) in xylene (30 ml) was heated under reflux for 3 hours and then allowed to cool. The solid was filtered off and crystallised from ethyl acetate to give 1-(2-hydroxy-5-methyl)benzylimidazole (4.36 g), m.p. 166°-167° C. Found: C, 70.19, H, 6.50, N, 14.94. $C_{11}H_{12}N_2O$ requires: C, 70.19, H, 6.43, N, 14.89%.

(B) 2-(1-Imidazolylmethyl)-4-methyl-phenoxyacetic acid ethyl ester (2-Hydroxy-5-methyl)benzylimidazole (5.64 g) was dissolved in dry N,N-dimethylformamide (50 ml) and sodium hydride (1.50 g, 50% dispersion in mineral oil) was added. The mixture was stirred at room temperature for 1 hour and then ethyl bromoacetate (5.04 g) was added over 10 minutes. The mixture was stirred at room temperature for 2 hours and then allowed to stand overnight before being poured into water. The resulting mixture was extracted with chloroform (2×150 ml) and the combined chloroform extracts were washed well with water and dried ($Na_2SO_4$). The solvent was evaporated and the mixture was triturated with petrol (b.p. 60°-80° C.) to give a solid (5.3 g) which was crystallised twice from ethyl acetate/petrol (b.p. 60°-80° C.) to give 2-(1-imidazolylmethyl)-4-methyl-phenoxyacetic acid ethyl ester, m.p. 86°-88° C. Found: C, 65.36, H, 6.63, N, 10.15. $C_{15}H_{13}N_2O_3$ requires: C, 65.67, H, 6.61, N, 10.21%.

EXAMPLE 2

2-(1-Imidazolylmethyl)-4-methyl-phenoxyacetic acid hydrochloride hemihydrate

A mixture of 2-(1-imidazolylmethyl)-4-methyl-phenoxyacetic acid ethyl ester (1.0 g) and 10 ml of 2.5 N sodium hydroxide solution was stirred at room temperature overnight. The solution was acidified with dilute hydrochloric acid and evaporated. The residue was extracted with boiling ethanol (2×50 ml) and the extracts were evaporated to give a solid which was crystallised from ethanol/ether to give 2-(1-imidazolylmethyl)-4-methyl-phenoxyacetic acid hydrochloride hemihydrate (0.50 g), m.p. 198°-201° C. Found: C, 53.69, H, 5.26, N, 9.45. $C_{13}H_{14}N_2O_3.HCl.\frac{1}{2}H_2O$ requires: C, 53.52, H, 5.53, N, 9.60%.

EXAMPLE 3

4-[2-(1-Imidazolylmethyl)-4-methyl-phenoxy]butyric acid ethyl ester hydrochloride This compound was prepared as described in Example 1B using ethyl 4-bromobutyrate instead of bromoacetate and a catalytic quantity of potassium iodide. The hydrochloride salt had an m.p. 101°-103° C. (from ethyl acetate). Found: C, 59.87, H, 6.84, N, 8.17. $C_{17}H_{22}N_2O_3.HCl$ requires: C, 60.35, H, 6.79, N, 8.27%.

EXAMPLE 4

4-[2-(1-Imidazolylmethyl)-4-methyl-phenoxy]butyramide

A mixture of 4-[2-(1-imidazolylmethyl)-4-methyl-phenoxy]butyric acid ethyl ester (1.0 g) and 0.880 ammonia solution was stirred for 6 hours and allowed to stand for a further 36 hours. The solid was filtered off and crystallised from water to give 4-[2-(1-imidazolyl-methyl)-4-methyl-phenoxy]butyramide (0.30 g), m.p. 114°–116° C. Found: C, 65.31, H, 7.23, N, 15.13. $C_{15}H_{19}N_3O_2$ requires: C, 65.91, H, 7.01, N, 15.37%.

EXAMPLE 5

4-[2-(1-Imidazolylmethyl)-4-methyl-phenoxymethyl]-benzoic acid

Treatment of (2-hydroxy-5-methyl)benzylimidazole with ethyl (4-bromomethyl)benzoate by the method of Example 1B gave 4-[2-(1-imidazolylmethyl)-4-phenoxy)benzoic]acid ethyl ester. A solution of the ester (4.17 g) in ethanol (40 ml) was treated with a solution of sodium hydroxide (2.0 g) in water (80 ml). The solution was heated under reflux for 1 hour and then allowed to stand at room temperature for 18 hours. The solution was evaporated to approximately half volume and just acidified with acetic acid. The precipitate was filtered off, washed with water and crystallised from ethanol to give 4-[2-(1-imidazolylmethyl)-4-methyl-phenoxymethyl]benzoic acid (2.33 g), m.p. 220°–221° C. Found: C, 70.34, H, 5.57, N, 8.59. $C_{19}H_{18}N_2O_3$ requires: C, 70.78, H, 5.63, N, 8.69%.

EXAMPLE 6

4-(1-Imidazolylmethyl)phenoxyacetic acid ethyl ester fumarate

Sodium hydride (3.17 g of 50% suspension in mineral oil) was added in portions to a stirred mixture of 1-(4-hydroxybenzyl) imidazole (11.50 g) in dry N,N-dimethyl-formamide (100 ml) at room temperature. The mixture was stirred at room temperature for 10 minutes and then heated to 100° C. for 30 minutes. It was then cooled and ethyl bromoacetate (11.04 g) was added dropwise with stirring. The resulting mixture was heated on a steam bath for 9 hours and then poured into water. The mixture was extracted with chloroform and the combined chloroform extracts were washed well with water and dried ($Na_2SO_4$). Evaporation of the solvent gave an oil which was chromatographed on silica gel. Elution with chloroform gave first some impurity and mineral oil followed by pure product. The product containing fractions were combined and evaporated to give an oil (13.90 g). A portion was dissolved in ether and the solution was treated with an excess of an ethereal solution of fumaric acid. The solid was filtered off and crystallised from ethyl acetate to give 4-(1-imidazolylmethyl)phenoxyacetic acid ethyl ester fumarate m.p. 99°–101° C. Found: C, 57.16; H, 5.29, N, 7.40. $C_{14}H_{16}N_2O_3.C_4H_4O_4$ requires: C, 57.44, H, 5.36, N, 7.44%.

EXAMPLE 7

4-(1-Imidazolylmethyl)phenoxyacetic acid hydrochloride

A solution of 4-(1-imidazolylmethyl)phenoxyacetic acid ethyl ester (6.0 g) in concentrated hydrochloric acid (10 ml) was heated at 100° C. for 8 hours and then evaporated to give an oil which solidified on trituration with ethyl acetate. The solid was crystallised twice from aqueous acetonitrile to give 4-(1-imidazolylmethyl)phenoxyacetic acid hydrochloride (4.84 g), m.p. 107°–110° C. Found: C, 50.24, H, 5.31, N, 9.83. $C_{12}H_{12}N_2O_3.HCl.H_2O$ requires: C, 50.28, H, 5.23, N, 9.77%.

EXAMPLE 8

4-(1-Imidazolylmethyl)phenoxyacetamide

A solution of 4-(1-imidazolylmethyl)phenoxyacetic acid ethyl ester (2.0 g) in ethanol (10 ml) and concentrated aqueous ammonia (SG 0.880) were heated under reflux for 2 hours and then evaporated. The residue was crystallised from a mixture of methanol and 2-butanone to give 4-(1-imidazolylmethyl)phenoxyacetamide (1.31 g) m.p. 173°–174° C. Found: C, 62.42, H, 5.76, N, 17.40. $C_{12}H_{13}N_3O_2$ requires: C, 62.32, H, 5.67, N, 18.17%.

EXAMPLE 9

N-Methyl-4-(1-Imidazolylmethyl)phenoxyacetamide

A solution of 4-(1-imidazolylmethyl)phenoxyacetic acid ethyl ester (1.02 g) in 33% ethanolic methylamine was allowed to stand for 24 hour. The solution was evaporated and the residue was crystallised from ethyl acetate/petrol to give N-methyl-4-(1-imidazolylmethyl)phenoxyacetamide (0.61 g), m.p. 124°–125° C. Found: C, 63.44, H, 6.21, N, 17.25. $C_{13}H_{15}N_3O_2$ requires: C, 63.66, H, 6.16, N, 17.13%.

EXAMPLE 10

1-[4-(Tetrazol-5-ylmethoxy)benzyl]imidazole

A. Sodium hydride (1.92 g of 50% dispersion in mineral oil was added portionwise to a stirred solution of 1-(4-hydroxybenzyl) imidazole (7.08 g) in dry N,N-dimethylformamide (100 ml) at 0° C. and the resulting mixture was stirred at room temperature for 1 hour. The mixture was cooled to 0° C. and chloroacetonitrile (2.96 g) was added over 2 minutes with stirring. The mixture was allowed to stand overnight and then evaporated. The residue was dissolved in chloroform and the mixture was filtered. The filtrate was evaporated and the residue was chromatographed on silica gel. Elution with chloroform gave initially mineral oil and impurity followed by pure product. Further pure product was obtained on changing the eluant to chloroform/methanol (9:1). The product-containing fractions were evaporated to give 4-(1-imidazolylmethyl)phenoxyacetonitrile (5.2 g) as an oil.

B. The nitrile (2.13 g), sodium azide (3.25 g) and ammonium chloride (2.67 g) were heated on a steam bath for 4 hours in N,N-dimethylformamide. The solution was then evaporated to dryness and a few ml. of water were added to the residue. The solid was collected by filtration and crystallised from ethanol to give 1-[4-(tetrazol-5-ylmethoxy)benzyl]imidazole (0.88 g), m.p. 189°–191° C. Found: C, 56.04, H, 4.73, N, 33.05. $C_{12}H_{12}N_6O$ requires: C, 56.2, H, 4.72, N, 32.80%.

EXAMPLE 11

A. 1-(4-Hydroxy-3-methoxy)benzylimidazole

A mixture of imidazole (20.4 g) and 4-hydroxy-3-methoxybenzyl alcohol (46.25 g) was heated at 160° C. for 2 hours. The resulting mixture was cooled and the product was crystallised twice from ethanol/petrol to give 1-(4-hydroxy-3-methoxy)benzylimidazole (48.7 g), m.p. 159°–160° C. Found: C, 64.73, H, 5.98, N, 13.70. $C_{11}H_{12}N_2O_2$ requires: C, 64.69, H, 5.90, N, 13.67%.

B. 4-(1-Imidazolylmethyl)-2-methoxyphenoxyacetic acid ethyl ester

Sodium hydride (3.8 g of 50% dispersion in mineral oil) was added portionwise to a stirred solution of 1-(4- hydroxy-3-methoxy)benzylimidazole (14.3 g) in dry N,N-dimethylformamide (150 ml) at 0° C. The mixture was stirred at room temperature for 1 hour and then cooled to 0° C. Ethyl bromoacetate (11.69 g) was added over 5 minutes with stirring and the mixture was stirred for 4 hours at room temperature. A few mls. of water was added to decompose excess sodium hydride and the mixture was evaporated. The residue was chromatographed on silica gel. Elution with chloroform gave mineral oil and some impurity. Elution with chloroform/ethanol (20:1) gave a solid which was crystallised from ethyl acetate/petrol to give 4-(1-imidazolylmethyl)-2-methoxyphenoxyacetic acid ethyl ester (9.02 g), m.p. 91° C. Found: C, 61.94, H, 6.26, N, 9.69. $C_{15}H_{18}N_2O_4$ requires: C, 62.05, W, 6.25, N, 9.65%.

EXAMPLE 12

4-(1-Imidazolylmethyl)-2-methoxyphenoxyacetamide

Treatment of 4-(1-imidazolylmethyl)-2-methoxyphenoxyacetic acid ethyl ester with ammonia as described in Example 8 gave 4-(1-imidazolylmethyl)-2-methoxyphenoxyacetamide, m.p. 124°–125° C. (from chloroform/petrol). Found: C, 59.39, H, 5.83, N, 16.07. $C_{13}H_{15}N_3O_3$ requires: C, 59.75, H, 5.78, N, 16.08%.

EXAMPLE 13

2-(1-Imidazolylmethyl)phenoxyacetic acid ethyl ester

Treatment of 2-(1-imidazolylmethyl)phenol with sodium hydride in dry N,N-dimethylformamide followed by ethyl bromoacetate as described in Example 11B gave 2-(1-imidazolylmethyl)phenoxyacetic acid ethyl ester as an oil which was used without further characterisation.

EXAMPLE 14

2-(1-Imidazolylmethyl)phenoxyacetic acid 2-(1-Imidazolylmethyl)phenoxyacetic acid ethyl ester (1 g) was heated on a steam bath for 30 minutes in a solution of potassium hydroxide (0.5 g) in water (10 ml) and the solution was allowed to stand at room temperature for 18 hours. The solution was then evaporated to small volume and acidified to pH 5 with acetic acid. The solid was collected by filtration and crystallised from water to give 2-(1-imidazolylmethyl)phenoxyacetic acid (0.26 g), m.p. 213°–214° C. Found: C, 51.83, H, 5.24, N, 12.34. $C_{12}H_{12}N_2O_3$ requires: C, 62.05, H, 5.21, N, 12.06%.

EXAMPLE 15

A. 1-(5-Chloro-2-hydroxy)benzylimidazole

A solution of 4-chloro-2-dimethylaminomethylphenol (30.0 g) and imidazole (11.75 g) in xylene (200 ml) was heated under reflux for 3.5 hours. The solution was evaporated and the residue was triturated with a little ethyl acetate to induce crystallisation. The product was crystallised from ethyl acetate/petrol to give 1-(5-chloro-2-hydroxy)benzylimidazole (15.91 g), m.p. 142°–144° C. Found: C, 57.33, H, 4.36, N, 13.45. $C_{10}H_9ClN_2O$ requires: C, 57.56, H, 4.35, N, 13.43%.

B. 4-Chloro-2-(1-imidazolylmethyl)phenoxacetic acid ethyl ester

Treatment of 1-(5-chloro-2-hydroxy)benzylimidazole with sodium hydride in dry N,N-dimethylformamide followed by ethyl bromoacetate as described in Example 11B gave 4-chloro-2-(1-imidazolylmethyl)phenoxyacetic acid ethyl ester, m.p. 108°–110° C. (from ethyl acetate/petrol). Found: C, 56.80, H, 4.83, N, 9.16. $C_{14}H_{15}ClN_2O_3$ requires: C, 57.06, H, 5.06, N, 9.51%.

EXAMPLE 16

4-Chloro-2-(1-imidazolylmethyl)phenoxyacetic acid

Hydrolysis of 4-chloro-2-(1-imidazolylmethyl)-phenoxyacetic acid ethyl ester by the method of Example 14 gave 4-chloro-2-(1-imidazolylmethyl)phenoxyacetic acid, m.p. 222°–224° C. (from water). Found: C, 53.95, H, 4.10, N, 10.52. $C_{12}H_{11}ClN_2O_3$ requires: C, 54.04, H, 4.16, N, 10.50%.

EXAMPLE 17

4-Chloro-2-(1-imidazolylmethyl)phenoxyacetamide

Treatment of 4-chloro-2-(1-imidazolylmethyl)-phenoxyacetic acid ethyl ester with ammonia as described in Example 8 gave 4-chloro-2-(1-imidazolylmethyl)phenoxyacetamide, m.p. 162°–164° C. (from isopropanol/petrol). Found: C, 53.91, H, 4.51, N, 15.79. $C_{12}H_{12}ClN_3O_2$ requires: C, 54.23, H, 4.57, N, 15.81%.

EXAMPLE 18

4-[2-(1-Imidazolylmethyl)phenoxy]butyric acid ethyl ester

Treatment of 1-(2-hydroxybenzyl)imidazole with sodium hydride followed by ethyl 4-bromobutyrate as described in Example 3 gave 4- 2-(1-imidazolylmethyl)-phenoxy butyric acid ethyl ester as an oil.

A portion of the product was dissolved in a small volume of ethanol and the solution was treated with an excess of a saturated diethyl ether solution of oxalic acid. The solid was filtered off and crystallised from ethyl acetate/petrol to give 4- 2-(1-imidazolylmethyl)-phenoxy butyric acid ethyl ester oxalate, m.p. 76°–81° C. Found: C, 56.76, H, 5.88, N, 7.43. $C_{16}H_{20}N_2O_3$ requires: C, 57.13, H, 5.86, N, 7.41%.

EXAMPLE 19

4-[2-(1-Imidazolylmethyl)phenoxy]butyric acid

Hydrolysis of 4-[2-(1-imidazolylmethyl)phenoxy]-butyric acid ethyl ester by the method of Example 14 gave 4-[2-(1-imidazolylmethyl)phenoxy]butyric acid, m.p. 150°–152° C. (from water). Found: C, 64.27, H, 6.29, N, 10.71. $C_{14}H_{16}N_2O_3$ requires: C, 64.59, H, 6.19, N, 10.76%.

EXAMPLE 20

4-[2-(1-Imidazolylmethyl)phenoxymethyl]benzonitrile

Treatment of 2-(1-imidazolylmethyl)phenol with sodium hydride and 4-bromomethylbenzonitrile in dry N,N-dimethylformamide by the method of Example 1B gave 4-[2-(1-imidazolylmethyl)phenoxymethyl]benzonitrile, m.p. 116°–118° C. (from ethyl acetate/petrol). Found: C, 74.64, H, 5.16, N, 14.65. $C_{18}H_{15}N_3O$ requires: C, 74.68, H, 5.22, N, 14.52%.

EXAMPLE 21

4-[2-(1-Imidazolylmethyl)phenoxymethyl]benzamide

4-[2-(1-Imidazolylmethyl)phenoxymethyl]benzonitrile (1.0 g) was dissolved in ethanol (10 ml) and 30% hydrogen peroxide (5 ml) was added followed by 6 N sodium hydroxide solution (5 ml). The mixture was heated at 50° C. for 1¾ hours and then evaporated to small volume. The solid was filtered off and crystallised from ethanol/petrol to give 4- 2-(1-imidazolylmethyl)- phenoxyethyl benzamide (0.60 g), m.p. 209°–211° C. Found: C, 69.97, H, 5.70, N, 13.28. C$_{18}$H$_{17}$N$_3$O$_2$ requires: C, 70.34, H, 5.57, N, 13.67%.

EXAMPLE 22

5-[4-(2-Imidazol-1-ylmethyl)phenoxymethyl]phenyltetrazole

Treatment of 4-[2-(1-imidazolylmethyl)phenoxymethyl]benzonitrile with sodium azide and ammonium chloride as described in Example 10 gave 5-[4-(2-imidazol-1-ylmethyl)phenoxymethyl]phenyltetrazole, m.p. 232°–234° C. (from methanol/ethyl acetate. Found: C, 64.74, H, 4.84, N, 25.69. C$_{18}$H$_{16}$N$_6$O requires: C, 65.06, H, 4.82, N, 25.30%.

EXAMPLE 23

A. 1-(2-Hydroxybenzyl)imidazole hydrobromide

A solution of 1-(3-methoxybenzyl)imidazole (18.1 g) in 48% hydrochloric acid (150 ml) was heated under reflux for 2 hours and then evaporated to give a thick oil. Trituration with diethyl ether gave a solid which was crystallised from isopropanol to give 1-(3-hydroxybenzyl)imidazole hydrobromide (19.25 g), m.p. 126°–128° C. Found: C, 46.46, H, 4.27, N, 11.17. C$_{10}$H$_{10}$N$_2$O.HBr requires: C, 47.07, H, 4.35, N, 10.98%.

B. 3-(1-Imidazolylmethyl)phenoxyacetic acid ethyl ester fumarate

Sodium hydride (3.2 g of 50% dispersion in mineral oil) was added portionwise to a stirred solution of 1-(3-hydroxybenzyl) imidazole hydrobromide (8.0 g) in dry N,N-dimethylformamide at 0° C. When the addition was complete the mixture was warmed briefly to 100° C. and cooled to room temperature. Ethyl bromoacetate (5.50 g) was added over 2 minutes with stirring and the resulting mixture was heated to 100° C. for 1.5 hours and then evaporated. The residue was partitioned between water and chloroform and the aqueous layer was separated.

The chloroform layer was dried (Na$_2$SO$_4$) and evaporated to give an oil which was chromatographed on silica gel. Elution with chloroform gave initially mineral oil and some impurity followed by pure product. Evaporation of the product containing fractions gave an oil (5.80 g).

A portion of the oil was dissolved in a little ethanol and an excess of a diethyl ether solution of fumaric acid was added. The solid was filtered off and crystallised from ethyl acetate to give 3-(1-imidazolylmethyl)-phenoxyacetic acid ethyl ester fumarate m.p. 85°–86° C. Found: C, 57.50, H, 5.35, N, 7.39. C$_{14}$H$_{16}$N$_2$O$_3$. C$_4$H$_4$O$_4$ requires: C, 57.44, H, 5.36, N, 7.44%.

EXAMPLE 24

3-(1-Imidazolylmethyl)phenoxyacetic acid hydrochloride

Hydrolysis of 3-(1-imidazolylmethyl)phenoxyacetic acid ethyl ester free base with concentrated hydrochloric acid according to the method of Example 7 gave 3-(1-imidazolylmethyl)phenoxyacetic acid hydrochloride, m.p. 179°–181° C. (from aqueous acetonitrile). Found: C, 52.23, H, 4.84, N, 10.65. C$_{12}$H$_{12}$N$_2$O$_3$.HCl requires: C, 53.64, H, 4.88, N, 10.43%.

EXAMPLE 25

4-(1-Imidazolylmethyl)phenoxyacetic acid hydrochloride (1 g) was added to distilled water (900 ml) and the pH adjusted to 5 with hydrochloric acid. Sodium chloride (18 g) was added and the solution made up to 2 liters. The final solution was sterilised by filtration through a bacteria-proof filter under aseptic conditions into 10 ml glass vials so as to comply with the test for sterility of Appendix 121 British Pharmacopea 1973.

EXAMPLE 26

Capsules are compounded from the following ingredients:

|  | mg/capsule |
|---|---|
| 4-(1-Imidazolylmethyl)phenoxyacetic acid HCl | 20 |
| Lactose | 250 |
| Maize starch | 75 |
| Magnesium stearate | 5 |
|  | 350 mg |

The ingredients are thoroughly blended, granulated and then filtered into hard gelatine capsules of the desired size.

We claim:

1. A compound of the formula

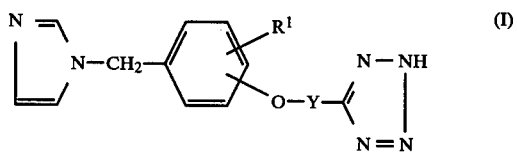

or a pharmaceutically acceptable acid addition salt thereof, wherein:
R$^1$ is hydrogen, C$_1$–C$_4$ lower alkyl, C$_1$–C$_4$ lower alkoxy or halogen; and
Y is (CH$_2$)$_n$ where n is an integer of from 1 to 4, or a group of the formula

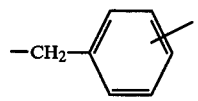

2. A compound of claim 1 wherein R$^1$ is hydrogen or methyl.

3. A compound of claim 1 or 2 wherein Y is methylene.

4. A compound of claim 1 or 2 wherein Y is benzyl.

5. A pharmaceutical composition for use as a selective inhibitor of thromboxane synthetase enzyme comprising a thromboxane synthetase enzyme inhibiting amount of a compound of claim 1 together with a pharmaceutically acceptable diluent or carrier.

6. A method of selectively inhibiting the action of the thromboxane synthetase enzyme in an animal which comprises administering to the animal a thromboxane synthetase inhibiting amount of a compound of claim 1 or of a pharmaceutical composition of claim 5.

* * * * *